(12) United States Patent
Zhuang et al.

(10) Patent No.: US 6,281,377 B1
(45) Date of Patent: Aug. 28, 2001

(54) SUBSTITUTED CYCLOALKENE NEW COPPER PRECURSORS FOR CHEMICAL VAPOR DEPOSITION OF COPPER METAL THIN FILMS

(75) Inventors: Wei-Wei Zhuang, Vancouver, WA (US); Tue Nguyen, Fremont, CA (US); Lawrence J. Charneski, Vancouver, WA (US); David R. Evans, Beaverton, OR (US); Sheng Teng Hsu, Camas, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 0 days.

(21) Appl. No.: 09/502,425

(22) Filed: Feb. 11, 2000

(51) Int. Cl.[7] ............................... C07F 1/08; C23C 16/00
(52) U.S. Cl. .................. 556/112; 556/117; 427/248.1
(58) Field of Search ................. 556/112, 117; 427/248.1

(56) References Cited

U.S. PATENT DOCUMENTS

| | | | |
|---|---|---|---|
| 4,385,005 | 5/1983 | Doyle | 260/464 |
| 4,425,281 | 1/1984 | Doyle | 260/430 |
| 5,085,731 | 2/1992 | Norman et al. | 156/646 |
| 5,096,737 | 3/1992 | Baum et al. | 427/38 |

OTHER PUBLICATIONS

Gerald Doyle, K. A. Eriksen and D. Van Engen, Organometallics 4, 830 (1985).

D. B. Beach et al., Low-temperature chemical vapor deposition of high purity copper from an organometallic source, Chem. Mater. (2) 216 (1990).

Hampden-Smith, M.J. et al., Chem. Mater. (2) 636 (1990).

Thomas H. Baum and Carl E. Larson, Chem. Mater. 4, 365 (1992).

Thomas H. Baum and Carl E. Larson, J. Electrochem. Soc. 140(1), 154 (1993).

*Primary Examiner*—Porfirio Nazario-Gonzalez
(74) *Attorney, Agent, or Firm*—David C. Ripma; Matthew D. Rabdau; Scott C. Krieger

(57) ABSTRACT

A method of forming a volatile copper precursor for chemical vapor deposition of copper metal thin film includes formation of a volatile liquid having a chemical formula of (n-R-m-cyclohexene)Cu(I)(hfac) or (n-R-m-cyclopentene)Cu(I)(hfac), where n,m=1–6, and where R is a alkyl, such as methyl and ethyl.

8 Claims, 1 Drawing Sheet

SUBSTITUTED CYCLOALKENE NEW COPPER PRECURSORS FOR CHEMICAL VAPOR DEPOSITION OF COPPER METAL THIN FILMS

FIELD OF THE INVENTION

This invention relates to the synthesis of volatile liquid copper precursors and their applications in chemical vapor deposition of copper metal thin films.

BACKGROUND OF THE INVENTION

Recently, there has been a great interest in chemical vapor deposition of copper metal thin films. Because of its low resistivity, ~1.7 $\mu\Omega$·cm, and high electromigration resistance, copper metal thin film material is considered to be ideal for use as metal interconnections in integrated circuits.

Chemical vapor deposition (CVD) of copper requires the use of a stable yet volatile precursor. For the purpose of commercialization, the cost of the copper precursor is an issue. In addition, the copper precursor must have good adhesion to metal nitride coated substrates, low resistivity, ~1.8 $\mu\Omega$·cm, excellent conformity to surface structures, and good electromigration resistance. In CVD processes, generally performed at elevated temperatures, the copper precursor must have a vapor pressure high enough to achieve a reasonable deposition rate, and must also be stable at deposition temperatures, without any decomposition in the CVD liquid delivery line or during vaporizer.

Copper metal thin films may be prepared via chemical vapor deposition using a variety of copper precursors. In 1990, D. B. Beach et al., Low-Temperature Chemical Vapor Deposition of High Purity Copper from an Organometallic Source, Chem. Mater. (2) 216 (1990), obtained pure copper films via CVD by using ($\eta^5$-$C_5H_5$)Cu($PMe_3$). At about the same time, Hampden-Smith, M. J. et al., Chem. Mater. (2) 636 (1990) declared the same results by using (tert-BuO)Cu($PMe_3$). These copper films, however, contain carbon and phosphorus, which elements constitute contaminants when used as interconnections in integrated circuits, and so they cannot be used as interconnectors in microprocessors. The studies of copper precursors conducted in the early of 1990's were concentrated on the evaluation of a series of copper(I) fluorinated $\beta$-diketonate complexes, which have been proven to be very promising sources for the use in the chemical vapor deposition of copper metal thin films.

Copper(I) fluorinated $\beta$-diketonate complexes were synthesized by Gerald Doyle, as described in U.S. Pat. No. 4,385,005, granted May 24, 1983, for Process for separating unsaturated hydrocarbons using copper or silver complexes with fluorinated diketonates, and U.S. Pat. No. 4,425,281, granted Jan. 10, 1984, for Copper or silver complexes with fluorinated diketones and unsaturated ligands, in which he presented the synthesis method and its application in the separation of unsaturated organic hydrocarbons.

U.S. Pat. No. 5,096,737, to Baum et al., granted Mar. 17, 1992, for Ligand Stabilization +1 Metal Beta-Diketonate Coordination Complexes and Their Use in Chemical Vapor Deposition of Metal Thin Films, described the application of copper(I)fluorinated $\beta$-diketonate complexes as copper precursors for CVD copper thin film preparation. Copper thin films have been prepared via chemical vapor deposition using these precursors. Among several liquid copper precursors, 1,5-dimethyl 1,5-cyclooctadiene copper(I) hexafluoroacetylacetonate mixed with 1,6-dimethyl 1,5-cyclooctadiene copper(I)hexafluoroacetylacetonate ((DMCOD)Cu(hfac)) and hexyne copper(I) hexafluoroacetylacetonate ((HYN)Cu(hfac)) were evaluated in detail. The copper thin films deposited using (DMCOD)Cu(hfac) have very good adhesion to metal or metal nitride substrates, but a high resistivity, i.e., ~2.5 $\mu\Omega$·cm, and a low deposition rate, whereas by using (HYN)Cu(hfac), the copper film has poor adhesion to a TiN substrate, and high resistivity, i.e., ~2.1 $\mu\Omega$·cm.

Another compound, 2-butyne copper(I)(hfac), ((BUY)Cu(hfac)), forms a copper film with low resistivity, ~1.93 $\mu\Omega$·cm, but has poor adhesion and is relatively expensive, and, because the compound is a solid, it must be vaporized prior to CVD.

The formation of copper(I)(hfac) stabilized with a series of trialkylvinylsilane (TMVS), as described in U.S. Pat. No. 5,085,731, to Norman et al., granted Feb. 4, 1992, for Volatile liquid precursors for the chemical vapor deposition of copper, results in improved copper thin films. Copper films, deposited using a liquid copper precursor of (hfac)Cu(TMVS) are of low resistivities and are reasonably adhesive to substrates. This liquid copper precursor has been used for the preparation of copper metal thin films via CVD for some time, but still has some drawbacks: stability, the poor adhesion of the copper film, and the cost of the trimethylvinylsilane stabilizer are significant impediments to the widespread use of this technique.

Other references of note are: Gerald Doyle, K. A. Eriksen and D. Van Engen, Organometallics 4, 830 (1985); Thomas H. Baum and Carl E. Larson, Chem. Mater. 4, 365 (1992); and Thomas H. Baum and Carl E. Larson, J. Electrochem. Soc. 140(1), 154 (1993).

SUMMARY OF THE INVENTION

A method of forming a volatile copper precursor for chemical vapor deposition of copper metal thin film includes formation of a volatile liquid having a chemical formula of (n-R-m-cyclohexene)Cu(I)(hfac) or (n-R-m-cyclopentene)Cu(I)(hfac), where n,m=1–6, and where R is a alkyl, such as methyl and ethyl.

An object of the invention is to provide a series of new high volatile liquid copper precursors for chemical vapor deposition of copper metal thin films.

Another object of the invention is to provide such precursors in an economical and stable form.

These and other objects and advantages of the invention will become more fully apparent as the description which follows is read in conjunction with the drawings.

DETAILED DESCRIPTION OF THE PREFERRED EMBODIMENTS

The invention involves the chemical vapor deposition (CVD) synthesis of a series of volatile copper precursors, to form copper metal thin films, and the synthesis of the precursors. The copper films deposited using these new liquid copper precursors exhibit excellent electrical properties, and good adhesion to metal and metal nitride substrates, such as W, Ti, TiN, Ta, TaN, Al, Pt, and the like.

To achieve the objects of this invention, a precursor must:
a. have a high volatile liquid phase and a high deposition rate of copper to form a copper thin film;
b. be stable at room temperature to provide easy storage and handling; and
c. have reasonable synthesis cost for commercialization.

Copper films prepared via CVD using this new copper precursor must:
a. have good adhesion to metal and metal nitride substrates, such as TiN, WN, TaN, etc.;
b. have low resistivity, <1.9 $\mu\Omega\cdot$cm;
c. have high electromigration resistance; and
d. have excellent conformity to extreme surface morphology.

The invention described herein includes the preparation of a new, highly volatile liquid thin metal copper precursor, known as (1-methyl-1-cyclohexene)-copper(I) hexafluoroacetylacetonate, or (1M1CH)Cu(I)(hfac). The price for 1-methyl-1-cyclohexene is approximately US$120.00 for 100 g, which is much lower than that of trimethylvinylsilane, used in the prior art, which generally costs about US$180.00 for 100 g. Experimental use of this precursor in CVD tests have proven that this new, highly volatile liquid copper thin metal precursor has the desired properties and meets all of the requirements listed above.

Figure 1:
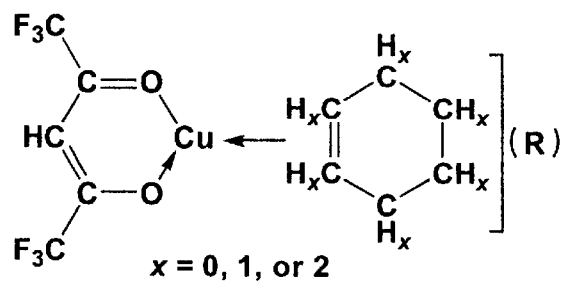
FIG. 1 depicts the structure of (n-R-m-cyclohexene)Cu(I)(hfac).
Figure 2:
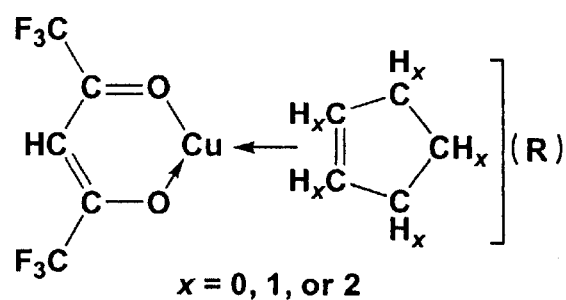
FIG. 2. depicts the structure of (n-R-m-cyclopentene)Cu(I)(hfac).
Figure 3:
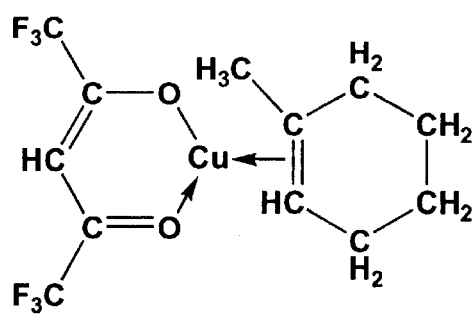
FIG. 3 depicts the structure of (1-methyl-1-cyclohexene)Cu(I)(hfac).

The copper films deposited using these new liquid copper precursors have exhibited excellent electrical properties, and good adhesion to metal and metal nitride substrates, such as W, Ti, TiN, Ta, TaN, Al, Pt, and the like. These organometallic copper complexes are represented by the structural formula (n-R-m-cyclohexene)Cu(I)(hfac), shown in FIG. 1, or (n-R-m-cyclopentene) Cu(I)(hfac), shown in FIG. 2, where (n,m=1–6), and where R is alkyl, such as methyl and ethyl. Preferably, the R is $CH_3$, whereby (1-methyl-1-cyclohexene)Cu(I)(hfac) compound is formed, as shown in FIG. 3.

All steps in the synthesis process are conducted in an air-free dry glovebox, or by using standard Schlenk techniques. Solvents are purified before synthesis. Dichloromethane is refluxed and distilled over calcium hydride under an atmosphere of nitrogen prior to use. 1-Methyl-1-cyclohexene and 1,1,1,5,5,5-hexafluoroacetylacetone, in the preferred embodiment, are supplied by Aldrich and Strem, respectively, and used as supplied, without further purification.

The synthesis procedure of organometallic copper(I) complexes is described in U.S. Pat. No. 4,385,005, supra, in which copper monoxide reacted with unsaturated organic hydrocarbon and 1,1,1,5,5,5-hexafluoroacetylacetone in dichloromethane or THF. The reaction is described by the following equation:

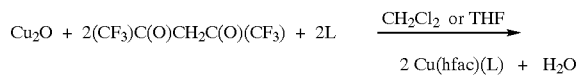

$$Cu_2O + 2(CF_3)C(O)CH_2C(O)(CF_3) + 2L \xrightarrow{CH_2Cl_2 \text{ or THF}} 2\ Cu(hfac)(L) + H_2O$$

where L is unsaturated organic hydrocarbon ligand.

Following the synthesis procedure described above, the synthesis of (1M1CH)Cu(hfac) results in a desired product, which, unfortunately, is not stable at room temperature over a long time. To resolve the stability issue, about 5% 1-methyl-1-cyclohexene (by product weight) is introduced into the product for stabilization. Following this procedure, and after letting the compound sit for one month, no solid precipitation was observed.

In the synthesis of (1M1CH)Cu(hfac), $Cu_2O$ in the amount of 41.26 g, (0.29 mol) is added to a 500 ml round bottom flask having 200 mL of $CH_2Cl_2$ therein. The flask is equipped with a stirring bar. To this $Cu_2O$ dichloromethane red solution, 57 mL of 1-methyl-1-cyclohexene, (0.48 mol) is added. The solution is stirred at room temperature for about five minutes. 100 g of 1,1,1,5,5,5-hexafluoroacetylacetone (0.48 mol) is introduced, with stirring. After one minute, the solution color gradually changes to green. The green solution is continually stirred for about another 10 minutes, and then filtered through celite, having a filter pore size of between about 10 $\mu$m and 25 $\mu$m.

The green filtrate is stripped under vacuum for two hours and then heated to 350° C., under vacuum, for another half-hour of stripping. This produces a green liquid organometallic copper compound containing a small number of little green crystals, which is then filtered through a fine filter (1 $\mu$m) to yield 145.7 g of product, having a yield of 82.64%, based on hfac. The theoretical yield based on H(hfac) is 176.3 g. For stabilization, 1-methyl-1-cyclohexene (6.437 g) was introduced into the product (138.621, total of 145.058 gram), in which the product contained 4.44% free 1-methyl-1-cyclohexene.

The NMR structural analysis was carried out on a QE 300 MHz NMR instrument. The results are as follows:

$^1$H NMR ($C_6D_6$) (1.22 (multi., 2, $C_6H_7H_2CH_3$), 1.30 (multi., 2, $C_6H_7H_2(CH_3)$), 1.41(s, 3, $C_6H_7H_2(CH_3)$), 1.75 (multi., 2, $C_6H_7H_2(CH_3)$), 1.80 (multi., 2, $C_6H_7H_2(CH_3)$), 4.79 (multi., 1, $C_6H8H(CH_3)$), 6.15 (s, 1, $CF_3C(O)CHC(O)CF_3$).

The results of copper metal thin film deposition via CVD using (1M1CH)Cu(hfac) liquid precursor were very good. The copper thin films have shown good adhesion to metal and metal nitride substrates, low resistivity, ~1.8 $\mu\Omega\cdot$cm, and very good reproducibility. The precursor is very volatile, and an extremely high deposition rate, approximately 500 Å per minute using 0.1 ml/min liquid injection rate at 50° C. of very low vaporizer temperature, has been achieved.

Thus, a new synthesis method has been employed for the synthesis of (1-methyl 1-cyclohexene)copper(I) (hexafluoroacetylacetonate). (1-methyl-1-cyclohexene) copper(I)(hexafluoroacetylacetonate) is a new liquid copper precursor, which is made stable at room temperature, by the inclusion of about 5% 1-methyl-1-cyclohexene as a stabilizer, and is highly volatile. Copper films prepared via chemical vapor deposition of (1-methyl-1-cyclohexene) copper(I) (hexafluoroacetylacetonate) have good adhesion to metal and metal nitride substrates and low resistivity. Copper films prepared via chemical vapor deposition using (1-methyl-1-cyclohexene) copper(I) (hexafluoroacetylacetonate) are useful and fully functional in IC devices.

Although a preferred embodiment of the invention, and several variations thereof have been disclosed, it will be appreciated that further variations and modifications may be made thereto without departing from the scope of the invention as defined in the appended claims.

We claim:

1. A method of forming a volatile liquid copper precursor for chemical vapor deposition of copper metal thin films, comprising:

placing 200 mL of $CH_2Cl_2$ in a vessel;

adding about 41.26 g (0.29 mol) of $Cu_2O$, thereby forming $Cu_2O$ dichloromethane red solution;

adding 57 mL (0.48 mol) of 1-methyl-1-cyclohexene;

stirring the solution at room temperature for about five minutes;

adding about 0.48 mol of a β-diketone;

stirring for about eleven minutes;

filtering the solution through celite, having a filter pore size of between about 10 μm and 25 μm;

stripping the solution, under vacuum, for about two hours;

heating the solution to about 35° C., under vacuum, and stripping for about 30 minutes;

filtering the solution through a fine filter having a pore size of about 1 μm; and adding about 5% to about 10%, by weight, of a stabilizing ligand.

2. The method of claim 1 wherein said adding about 0.48 mol of a β-diketone includes adding about 100 g of 1,1,1,5,5,5-hexafluoroacetylacetone.

3. A method of forming a volatile copper precursor for chemical vapor deposition of copper metal thin film, comprising:

forming a volatile liquid having a chemical formula taken from the group of chemical formulas consisting of (1-R-1-cyclohexene)Cu(I)(hfac) and (1-R-1-cyclopentene)Cu(I)(hfac), where R is a alkyl, taken from the group of alkyls consisting of methyl and ethyl.

4. The method of claim 3 which includes adding a stabilizing ligand.

5. The method of claim 4 wherein said adding a stabilizing ligand includes adding 1-methyl-1-cyclohexene.

6. The method of claim 5 wherein said adding 1-methyl-1-cyclohexene includes adding about 5% to 10% of 1-methyl-1-cyclohexene by weight.

7. The method of claim 3 which further includes adding a β-diketone.

8. The method of claim 7 wherein said adding a β-diketone includes adding 1,1,1,5,5,5-hexafluoroacetylacetone.

* * * * *